US00PP20624P3

(12) United States Plant Patent

Dozier, Jr. et al.

(10) Patent No.: US PP20,624 P3

(45) Date of Patent: Jan. 5, 2010

(54) CHESTNUT PLANT NAMED 'AU BUCK IV'

(50) Latin Name: *Catanea mollissima*
Varietal Denomination: AU BUCK IV

(75) Inventors: W. Alfred Dozier, Jr., Opelika, AL (US); Joseph Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,112

(22) Filed: Jan. 30, 2008

(65) Prior Publication Data

US 2009/0193553 P1 Jul. 30, 2009

(51) Int. Cl.
*A01H 5/00* (2006.01)

(52) U.S. Cl. ..... Plt./152

(58) Field of Classification Search ..... Plt./152
See application file for complete search history.

(56) References Cited

PUBLICATIONS

Lin ye ke ji et al., "Forest science & Technology", Jan. 1989, pp. 16–18, Baker Auxiliary Stacks SD1.L56, No. 2–1990.
Crane, H. L. et al., Nut Breeding', U.S. Department of Agriculture Yearbook, Jan. 1937, pp. 827–837.
Hemming, E. Sam, "Chinese Chesnut in Maryland", Jan. 1944, pp. 32–34, A.R. Northern Nut Growers Assoc.
Kim, Kap Duk et al., Studies On The Farmers Cultivating Chestnut Orchards in Korea and Its Financial Analysis, Jan. 1971, pp. 51–74, Bull. Seol. Nut Univ.Fores., No. 8.
Snare, Lester, Chestnuts Production', Jan. 1996, pp. 422–427, NSW Agriculture, Agfact H3.1.50., http://www.n-rdc.gov.au/pub/handbook/chestnuts.pdf.
Harris, Hubert et al., Three Chinese Chestnuts: Au–Cropper, Au–Leader, and Au–Homestead–Their History and Production', Mar. 1980, pp. 3–8, Agricultural Experiment Station Auburn University Circular 247.
Jaynes, Richard A. et al., "Handbook of North American Nut Trees", pp. 264–286, The W.F. Humphrey Press, Inc. New York.

*Primary Examiner*—Annette H Para
(74) *Attorney, Agent, or Firm*—Haverstock & Owens LLP

(57) ABSTRACT

'AU Buck IV' is a new and distinct Chinese chestnut cultivar that is blight resistant, precocious and an annual bearer. It produces a medium to heavy crop load each year and a large sized nut. Nut drop begins about October 10 and continues for a 5–6 week period. A high percentage of nuts produced drop during the first 4 weeks of the period that nuts drop from this cultivar. 'AU Buck IV' is a small tree that is broadly elliptic in shape with high, upright to spreading and diffuse branches that was 8.23 meters tall with a canopy covering an area of 30.19 square meters at 15 years old. 'AU Buck IV' is the fourth cultivar to mature and drop nuts in a series of four Chinese chestnut cultivars that will provide for a continuous nut drop of a high energy wildlife food source from late August through mid-to-late November.

3 Drawing Sheets

Latin name of the genus and species of the plant claimed: *Castanea mollissima* Blume.
Variety denomination: 'AU Buck IV'.

BACKGROUND OF THE INVENTION

A Chinese chestnut planting was established at Auburn University, Auburn, Ala., from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000 seedlings. A planting of third generation seedlings from controlled mass pollination of 'AU Leader', 'AU Homestead' and 'AU Cropper' was established at the Auburn University Piedmont Substation at Camp Hill, Ala.

SUMMARY OF THE INVENTION

'AU Buck IV' is an open pollinated seedling of 'AU Cropper'.

The present invention relates to a new and distinct Chinese chestnut cultivar that is blight resistant, precocious and produces a medium to large crop annually for tree size. 'AU Buck IV' is a late maturing cultivar from which nuts starts dropping about October 10 and continues for a 5 to 6 week period. A high percent of the nuts produced drop during the first 3 weeks of the period that nuts drop from this cultivar. Nut size is large and average nut weight is 15.5 g. The large nut is an excellent high energy food source for wildlife such as deer and squirrels in late fall. The 15-year old original tree of 'AU Buck IV' is a small tree. It is 8.23 meters tall, has a canopy width of 6.20 meters and a canopy area of 30.19 square meters. The original tree of 'AU Buck IV' cultivar has produced a medium to heavy crop load for tree size each season and produced 19.8 kg (43.6 pounds) of nuts in 2006. There has been no evidence of insect or disease damage to the tree, foliage or nuts.

'AU Buck IV' cultivar is the fourth cultivar to mature and drop nuts in a series of four Chinese chestnut cultivars that will provide for a continuous nut drop of a high energy wildlife food source from late August through mid-to-late November. 'AU Buck I', 'AU Buck II' and 'AU Buck III' are the other three cultivars, which are disclosed in U.S. patent application Ser. No. 12/012,091, filed on Jan. 30, 2008, and entitled "CHESTNUT PLANT NAMED 'AU BUCK I'", U.S. patent application Ser. No. 12/012,025, filed on Jan. 30, 2008, and entitled "CHESTNUT PLANT NAMED 'AU BUCK II'" and U.S. patent application Ser. No. 12/012,110, filed on Jan. 30, 2008, and entitled "CHESTNUT PLANT NAMED 'AU BUCK III'", which are hereby incorporated by reference.

The new cultivar is able to be asexually reproduced by budding or grafting onto a seedling Chinese chestnut rootstock. The unique characteristics come true to form and are established and transmitted through asexual propagation.

DETAILED BOTANICAL DESCRIPTION

Figure 1:
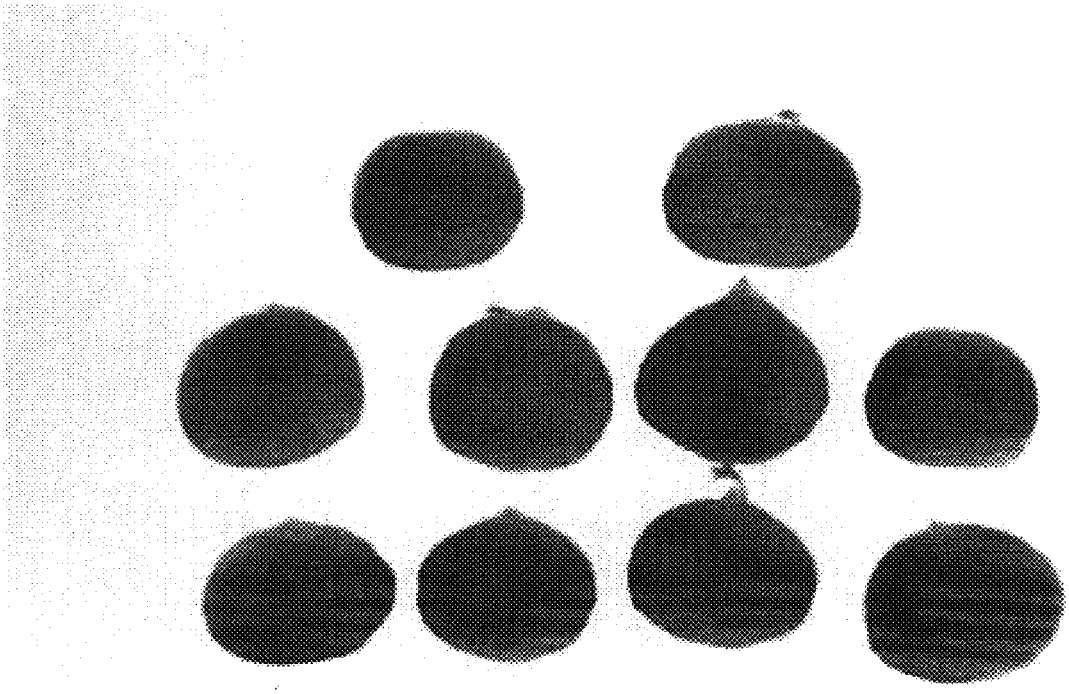
FIG. 1 is a photograph of nuts of the 'AU Buck IV' cultivar.
Figure 2:
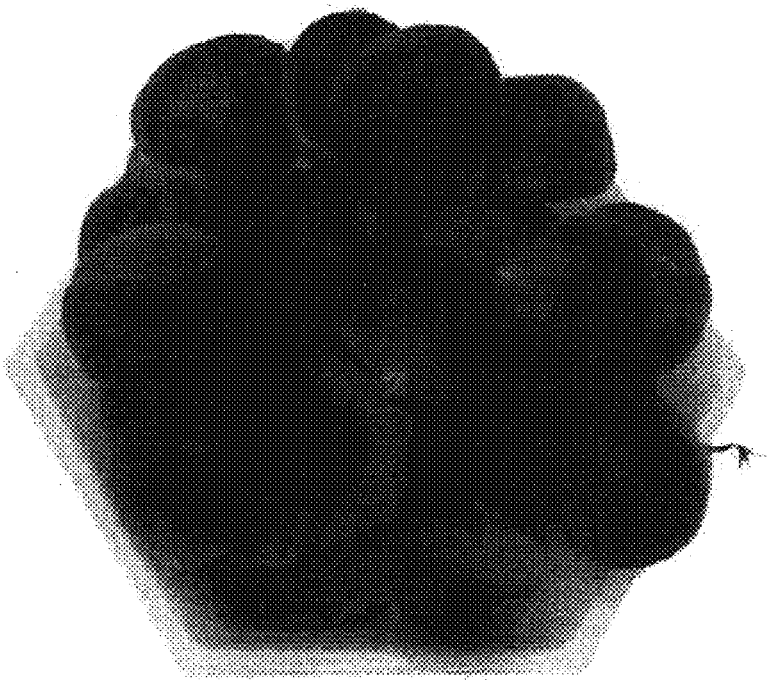
FIG. 2 is a photograph of nuts of the 'AU Buck IV' cultivar.
Figure 3:
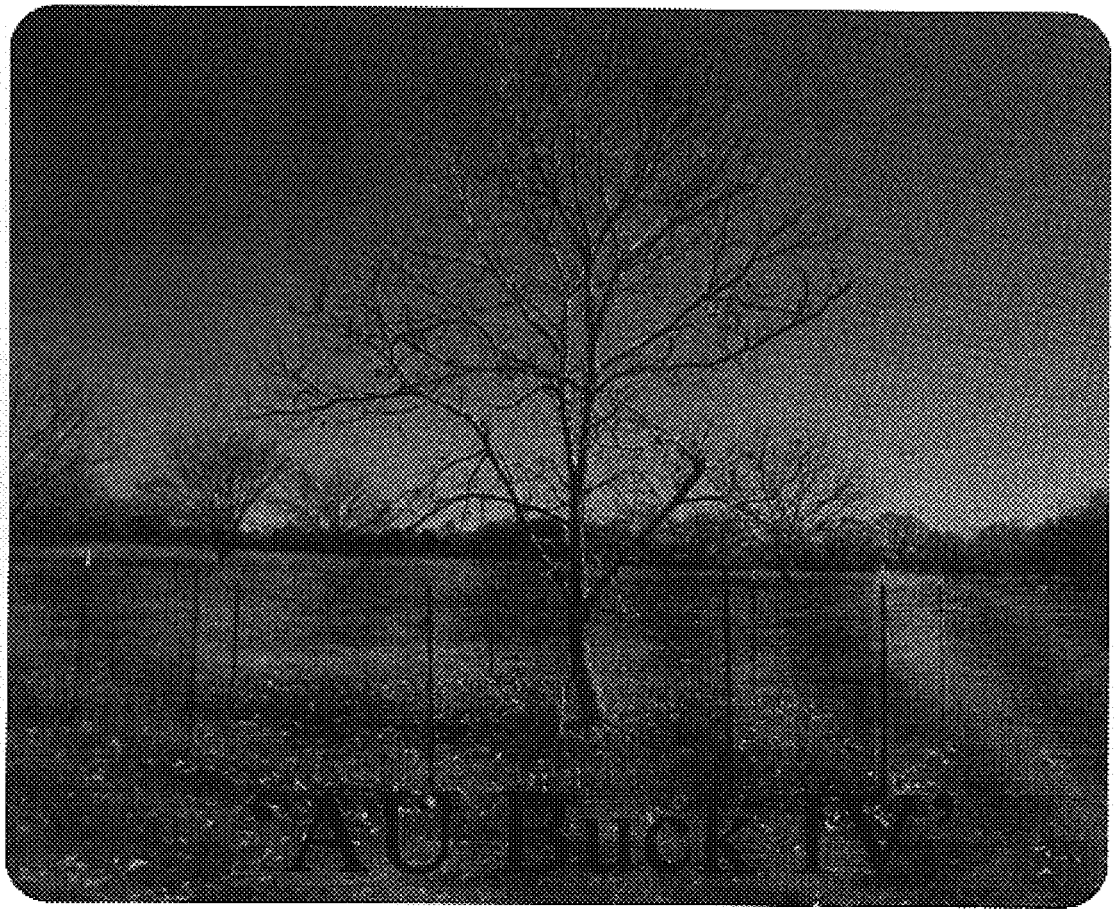
FIG. 3 is a photograph of a tree of the 'AU Buck IV' cultivar.

The Chinese chestnut, *Castanea mollissima* Blume, is a cold hardy temperate zone species native to China. It can be grown between 30° and 50° latitudes. The Chinese chestnut is resistant to chestnut blight fungus *Cryphonectria parasitica*. Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker and, in general, mature leaves are broader than those of other species. The nuts have a small scar or hilum. The pellicle or thin membranous skin on the nuts is thin and peels readily from the kernel. The trees are a spreading type and long-lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on lower part of the upper staminate catkins and rarely on separate catkins usually 3 in a prickly symmetrical involucre with 7–9 styles and a 6-celled ovary. Nuts are small, brown with a pale scar at the base. Generally, 1–3 nuts per involucre or bur are present.

'AU Buck IV' is a small tree that is broadly elliptic in shape with high, upright to spreading, and diffuse branches. The original 15-year old 'AU Buck IV' tree is 8.23 meters (26.75 feet) tall with a trunk diameter at breast height of 19.5 cm (7.18 inches). The canopy is 6.20 meters (20.33 feet) wide and covers a canopy area of 30.19 square meters (324.97 square feet). 'AU Buck IV' produces a large nut that has a 5 year average weight of 15.5 g, length of 30.0 mm (1.18 inches) and width of 34.0 mm (1.34 inches). The nuts start dropping about October 10 and continues to drop for a 5–6 week period. A high percent of the nuts produced drop during the first 4 weeks of the period that nuts drop from this cultivar. 'AU Buck IV' is a small tree that is precocious, fruits annually, and produces a good crop for the tree size, and drops the nuts over an extended time period.

In the planting at the Piedmont Substation, Camp Hill, Ala., accurate yields could not be obtained due to extremely heavy wildlife (deer and turkey) feeding. Therefore, the trees were rated for crop load each year. The crop load on 'AU Buck IV' has been rated as medium to heavy for the small sized tree. In the fall of 2006, individual trees were caged with 6 foot (1.83 meters) tall chicken wire prior to nut drop to exclude wildlife and nuts were picked up daily during nut drop. The 15-year old 'AU Buck IV' tree produced 19.8 kg (43.6 pounds) of nuts in 2006. This yield is about equal to the reported yields for similar aged trees.

The table below illustrates the specific differences between the 'AU Buck IV' cultivar and the 'Revival' cultivar.

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and Chroma (spectrophotometer model CM-2002; Minolta Camera Co., Japan).
'AU BUCK IV' CHESTNUT Tree:

Size (at maturity) - small - fifteen year old original tree is 8.23 meters tall with a canopy width of 6.20 meters and a canopy area of 30.19 sq. meters
Tree shape is broadly elliptic.
Vigor - moderately vigorous Trunk:

Form - upright with branches high and diffuse
Texture - relatively smooth
Color of bark - brown RHS N200B, Chroma C* 9.96, hue angle 88.61

Branches:

Form - upright to spreading
Texture - relatively smooth
Lenticels - few, small
Branching habit - high and diffuse
Color - new wood; grey-brown, RHS N199B, Chroma C* 15.74, hue angle 77.23, mature wood: greyed-green RHS 197A
Chroma C* 11.43, hue angle 92.03

Foliage:

Quantity - abundant
Density - dense

Leaves:

Size - large. Length (cm) 16.8 (13.5-20.0) [20]
width (cm) 7.6 (6.2-8.9) [20]
leaf ratio 2.2(1.9-2.6) [20]
Shape - broadly elliptic to oblong occasionally obovate
leaf tip - acute
leaf base - rounded, equal to oblique
Thickness - thick. leaf venation 1° pinnate: 2° ± parallel, moderately prominent abaxially
Texture - strongly coriaceous
Margin - weakly to moderately serrate, teeth ascending
Petiole - length 1.0 cm (0.5-1.51) [20]
Petiole pubescence- glabrous to sparsely simple hairs
Color- adaxial surface, glabrous blade, sparse simple hairs on veins medium green, highly shiny, RHS 147A,
Chroma C* 16.61, hue angle 118.30
abaxial surface, moderately to densely stellate hairs on blade, sparse simple hairs on blade, RHS 148B, Chroma C* 19.77, hue angle 109.47

Bloom:

Amount of bloom - heavy
Color - at anthesis, 161D greyed-yellow group, 157D green-white group, 155C white group
Blooming period - mid-May. After foliation in April.
Age at which tree starts flowering - early, 2-3 years after graft replacement.
Male flower - Catkin length (cm) - 13.2 (9.0-15.3) [15]
Male flower- stamen number per catkin - 11.6 (10.0-12.0) [15]
Female flower - flower number per bur - 3
Female flower - style number per flower 7.7 (6-9) [15]

-continued

Crop:

Bearing - regular annual bearer
Productivity - prolific
Ripening period - long, nuts begins dropping about October 10 and continues for a 5-6 week period.
Distribution of nuts on tree - well distributed, fruits on terminals with 2-4 burs per terminal.
Tenacity - burs crack while on tree and nuts release and drop from bur.
Hull:

Description - spiny round bur
Size - 2.18-3.02" in diameter
Number of nuts - 2-3 per bur
Dehiscence - splits easily when still on tree
Color - yellow-green at dehiscence, RHS N144C
Nut:

Size - large. Average size - 1.18" × 1.34" × 0.87". Average weight - 15.5 grams 29 (23-35) nuts per pound.
Form - flattened on 1 side. occ. 2, hemispheric to somewhat ovoid on other side
Blossom end - broadly rounded with an obtuse tip
Basal end - broadly rounded to flat
Color - light brown, RHS 200B. Chroma C* 10.18, hue angle 43.00
Pubescence- mixed long and short, fine, white hairs densely covering ¼ to ⅓ of the distal end, otherwise glabrate to glabrous elsewhere
Shell - thin
Hardness of shell - relatively hard, yet not rigid
Texture of shell - smooth
Percentage of kernel to nut - very high-90-95%
Kernel:

Size - almost as large as nut size
Form - same as nut shape
Pellicle - thin
Flavor - excellent, very sweet
Color - light-straw color, RHS 162A, Chroma C* 47.61, hue angle 81.36
Resistance to insects: no unusual susceptibilities noted
Resistance to disease: no susceptibilities to disease noted
The chestnut tree and its nuts herein described may vary in slight detail due to climatic and soil conditions under which the variety may be grown; the present description being of the variety as grown in Camp Hill, Ala.

The botanical details of this variety of chestnut tree - with color definitions (except those in common color terms) referenced to Maerz and Paul Dictionary of Color - are as follows:
'REVIVAL'

Tree:

Size (at maturity) - large
Vigor - very vigorous
Trunk;

Form - upright with branches spreading in upper reaches of tree.
Texture - relatively smooth
Color of bark - Silvergray (13-A-1)
Branches:

Form - strong
Texture - relatively smooth
Lenticels - few, small
Branching habit - spreading in upper region of tree
Color - new wood: reddish brown and glossy, mature wood: silver gray
Foliage:

Quantity - abundant
Density - dense
Leaves:

Size - large. Average length - 5-7" (including petiole).
Average width - 2"

-continued

Shape - oblong with acute tip and rounded base
Thickness - thick
Texture - smooth
Margin - dentate
Petiole - length: medium. Thickness: medium.
Color - Top side - glossy dark green (22-L-12).
Under side- lighter green (21-D-7).
Bloom:

Amount of bloom - heavy
Color - cream white (17-B-1)
Blooming period - late. After leaf out in April
Age at which tree starts flowering - early; 2-3 years years after graft replacement.
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parasitica*), no other susceptibilities to any other disease
The chestnut tree and its nuts herein described may vary in slight detail due to climatic and soil conditions under which the variety may be grown; the present description being of the variety as grown in Alachua, Fla.

'AU Buck IV' is different from 'AU Gobbler I' in several ways. For example, the size of the trees, the trunk forms and colors, the branches, the leaves, the crop and the nuts have differences. Specifically, the 'AU Buck IV' tree is shorter with a canopy width and a canopy area smaller than the 'AU Gobbler I' tree. The 'AU Buck IV' branches are upright to spreading and grey brown (new) or greyed-green (mature); whereas, the 'AU Gobbler I' branches are upright and brown (new) or greyed-green (mature). The leaves differ in size, shape, texture, margin and color. The ripening period for the 'AU Buck IV' is around October 10 and continues for a 5–6 week period, but the 'AU Gobbler I' ripening period is around August 25 and continues for 4–5 weeks. The average weight of the nuts of 'AU Buck IV' is 15.5 grams versus 7.7 grams for 'AU Gobbler I'. Furthermore, 'AU Buck IV' has roughly 29 nuts per pound, and 'AU Gobbler I' has roughly 59 nuts per pound.

'AU Buck IV' is different from 'AU Gobbler II' in several ways. For example, the trees, the trunk colors, the branch colors, the leaves, the crop and the nuts have differences. Specifically, the 'AU Buck IV' tree is taller with a canopy width and canopy area smaller than the 'AU Gobbler II' tree. The 'AU Buck IV' branches are grey-brown (new) or greyed-green (mature); whereas, the 'AU Gobbler II' branches are brown (new) or greyed-green (mature). The leaves differ in size, shape margin and color. The ripening period for the 'AU Buck IV' is around October 10 and continues for a 5–6 week period, but the 'AU Gobbler II' ripening period is around September 5 and continues for 4–5 weeks. The average weight of the nuts of 'AU Buck IV' is 15.5 grams versus 5.7 grams for 'AU Gobbler II'. Furthermore, 'AU Buck IV' has roughly 29 nuts per pound, and 'AU Gobbler II' has roughly 65–101 nuts per pound.

'AU Buck IV' is different from 'AU Premier' in several ways. For example, the trees, the trunk colors, the branch colors, the leaves, the crop and the nuts have differences. Specifically, the 'AU Buck IV' tree is taller with a canopy width larger than the 'AU Premier' tree. The 'AU Buck IV' has a brown trunk, and the 'AU Premier' has a greyed-green trunk. The 'AU Buck IV' branches are grey-brown (new) or greyed-green (mature); whereas, the 'AU Premier' branches are brown (new) or greyed-green (mature). The leaves differ in size, shape, thickness, texture, margin and color. The ripening period for the 'AU Buck IV' is around October 10, and the 'AU Premier' ripening period is early September through mid-November. The average weight of the nuts of 'AU Buck IV' is 15.5 grams versus 1.26 grams for 'AU Premier'. Furthermore, 'AU Buck IV' has roughly 29 nuts per pound, and 'AU Premier' has roughly 360.3 nuts per pound.

'AU Buck IV' is different from 'AU Encore' in several ways. For example, the trees, the trunk colors, the branch colors, the leaves, the crop and the nuts have differences. Specifically, the 'AU Buck IV' tree is taller with a canopy area smaller than the 'AU Encore' tree. The 'AU Buck IV' has a brown trunk, and the 'AU Encore' has a greyed-green trunk. The 'AU Buck IV' branches are grey-brown (new) or greyed-green (mature); whereas, the 'AU Encore' branches are brown (new) or greyed-green (mature). The leaves differ in size, shape, thickness, texture, margin, petiole and color. The ripening period for the 'AU Buck IV' is around October 10, but the 'AU Encore' ripening period is late September through late November. The average weight of the nuts of 'AU Buck IV' is 15.5 grams versus 2.4 grams for 'AU Encore'. Furthermore, 'AU Buck IV' has roughly 29 nuts per pound, and 'AU Encore' has roughly 189.2 nuts per pound.

What is claimed is:

1. A new and distinct cultivar of the species *Castanea mollissima* Blume named 'AU Buck IV' as described and illustrated herein.

* * * * *

'AU Buck IV'

'AU Buck IV'

UNITED STATES PATENT AND TRADEMARK OFFICE

CERTIFICATE OF CORRECTION

PATENT NO. : PP 20,624 P3
APPLICATION NO. : 12/012112
DATED : January 5, 2010
INVENTOR(S) : W. Alfred Dozier, Jr., Joseph Daniel Norton and Curtis J. Hansen It is certified that error appears in the above-identified patent and that said Letters Patent is hereby corrected as shown below:

IN THE SPECIFICATION

At the title page (50), please replace Latin Name: *Catanae mollissima* with *Castanea mollissima*

Signed and Sealed this

Sixteenth Day of March, 2010

David J. Kappos

David J. Kappos
*Director of the United States Patent and Trademark Office*